(12) United States Patent
Kiely et al.

(10) Patent No.: US 9,505,882 B2
(45) Date of Patent: Nov. 29, 2016

(54) HYDROXYPOLYAMIDE GEL FORMING AGENTS

(71) Applicant: THE UNIVERSITY OF MONTANA, Missoula, MT (US)

(72) Inventors: Donald E. Kiely, Missoula, MT (US); Tyler N. Smith, Missoula, MT (US)

(73) Assignee: THE UNIVERSITY OF MONTANA, Missoula, MT (US)

( * ) Notice: Subject to any disclaimer, the term of this patent is extended or adjusted under 35 U.S.C. 154(b) by 0 days.

(21) Appl. No.: 15/068,964

(22) Filed: Mar. 14, 2016

(65) Prior Publication Data

US 2016/0194446 A1  Jul. 7, 2016

Related U.S. Application Data

(63) Continuation of application No. 14/107,297, filed on Dec. 16, 2013, now Pat. No. 9,315,624, which is a continuation of application No. 12/272,732, filed on Nov. 17, 2008, now Pat. No. 8,623,943.

(60) Provisional application No. 61/003,444, filed on Nov. 15, 2007.

(51) Int. Cl.

| | |
|---|---|
| C08G 69/26 | (2006.01) |
| C08G 69/28 | (2006.01) |
| C08J 3/075 | (2006.01) |
| A01N 25/04 | (2006.01) |
| A61K 47/34 | (2006.01) |
| C05G 3/00 | (2006.01) |
| C08K 3/22 | (2006.01) |
| C08K 3/26 | (2006.01) |
| C08K 3/28 | (2006.01) |
| C08K 3/32 | (2006.01) |
| C08K 5/05 | (2006.01) |
| C08K 5/21 | (2006.01) |
| C08K 5/41 | (2006.01) |
| C08L 5/00 | (2006.01) |
| C08L 77/06 | (2006.01) |
| C08L 89/00 | (2006.01) |
| C05B 7/00 | (2006.01) |
| C05C 5/02 | (2006.01) |
| C05C 9/00 | (2006.01) |

(52) U.S. Cl.
CPC ............ *C08G 69/26* (2013.01); *A01N 25/04* (2013.01); *A61K 47/34* (2013.01); *C05B 7/00* (2013.01); *C05C 5/02* (2013.01); *C05C 9/00* (2013.01); *C05G 3/0064* (2013.01); *C05G 3/0076* (2013.01); *C08G 69/265* (2013.01); *C08G 69/28* (2013.01); *C08J 3/075* (2013.01); *C08K 3/22* (2013.01); *C08K 3/26* (2013.01); *C08K 3/28* (2013.01); *C08K 3/32* (2013.01); *C08K 5/05* (2013.01); *C08K 5/21* (2013.01); *C08K 5/41* (2013.01); *C08L 5/00* (2013.01); *C08L 77/06* (2013.01); *C08L 89/00* (2013.01); *C08J 2377/06* (2013.01); *C08K 2003/324* (2013.01); *C08L 2201/54* (2013.01); *C08L 2201/56* (2013.01)

(58) Field of Classification Search
CPC .... C08G 69/26; C08G 69/265; C08G 69/28; C08G 3/0064; C08J 3/075; A01N 25/04; A61K 47/34
See application file for complete search history.

(56) References Cited

U.S. PATENT DOCUMENTS

| | | |
|---|---|---|
| 1,520,885 A | 12/1924 | Rankin |
| 2,314,831 A | 3/1943 | Kamlet |
| 2,380,196 A | 7/1945 | Solomon |
| 2,419,019 A | 4/1947 | Hales |
| 2,436,659 A | 2/1948 | Mehltretter et al. |
| 2,472,168 A | 6/1949 | Mehltretter |
| 2,529,177 A | 11/1950 | Nieland |
| 2,529,178 A | 11/1950 | Nieland |
| 3,242,207 A | 3/1966 | Ulrich et al. |
| 3,346,623 A | 10/1967 | Young |
| 3,362,885 A | 1/1968 | Harned |
| 3,589,859 A | 6/1971 | Foroulis |
| 3,652,396 A | 3/1972 | Tanaka |
| 3,696,044 A | 10/1972 | Rutledge |
| 3,711,246 A | 1/1973 | Foroulis |

(Continued)

FOREIGN PATENT DOCUMENTS

| | | |
|---|---|---|
| CA | 2188063 | 4/1998 |
| CN | 1131651 | 9/1996 |

(Continued)

OTHER PUBLICATIONS

United States Co-pending U.S. Appl. No. 15/133,699 by Smith et al., filed Apr. 20, 2016.

(Continued)

*Primary Examiner* — John Uselding
(74) *Attorney, Agent, or Firm* — Lisa V. Mueller; Michael Best & Friedrich LLP

(57) ABSTRACT

Hydroxypolyamides, hydroxypolyamide products, and post-hydroxypolyamides are disclosed as gel forming agents. Hydroxypolyamides and post-hydroxypolyamides are prepared from known methods. Hydroxypolyamide products are produced from a modified polymerization procedure which utilizes strong base for deprotonation of ammonium salts from the esterification of stoichiometrically equivalent polyacid:polyamine salts. The hydroxypolyamide products are capable of gel formation at lower concentrations than hydroxypolyamides and post-hydroxypolyamides from the known methods of preparation, and are therefore superior gel forming agents.

9 Claims, No Drawings

(56) References Cited

U.S. PATENT DOCUMENTS

| | | |
|---|---|---|
| 3,798,168 A | 3/1974 | Tumerman et al. |
| 3,819,659 A | 6/1974 | Baldwin et al. |
| 3,951,877 A | 4/1976 | Okumura et al. |
| 4,000,083 A | 12/1976 | Heesen |
| 4,102,799 A | 7/1978 | Finck |
| 4,108,790 A | 8/1978 | Foroulis |
| 4,120,655 A | 10/1978 | Crambes |
| 4,129,423 A | 12/1978 | Rubin |
| 4,485,100 A | 11/1984 | Hochstrasser et al. |
| 4,512,552 A | 4/1985 | Katayama et al. |
| 4,833,230 A | 5/1989 | Kiely et al. |
| 4,834,793 A | 5/1989 | Schneider et al. |
| 4,845,123 A | 7/1989 | Walaszek |
| 5,017,485 A | 5/1991 | Bringer-Meyer |
| 5,256,294 A | 10/1993 | van Reis |
| 5,264,123 A | 11/1993 | Bailey |
| 5,279,756 A | 1/1994 | Savio et al. |
| 5,312,967 A | 5/1994 | Kiely et al. |
| 5,329,044 A | 7/1994 | Kiely et al. |
| 5,330,683 A | 7/1994 | Sufrin |
| 5,364,644 A | 11/1994 | Walaszek |
| 5,376,499 A | 12/1994 | Hammerschmidt et al. |
| 5,434,233 A | 7/1995 | Kiely et al. |
| 5,473,035 A | 12/1995 | Kiely et al. |
| 5,478,374 A | 12/1995 | Kiely |
| 5,531,931 A | 7/1996 | Koefed |
| 5,561,160 A | 10/1996 | Walaszek |
| 5,562,828 A | 10/1996 | Olsen et al. |
| 5,599,977 A | 2/1997 | Kiely et al. |
| 5,891,225 A | 4/1999 | Mishra |
| 5,958,867 A | 9/1999 | Lamberti et al. |
| 5,999,977 A | 12/1999 | Riddle |
| 6,049,004 A | 4/2000 | Kiely et al. |
| 6,156,226 A | 12/2000 | Klyosov et al. |
| 6,228,825 B1 | 5/2001 | Gorlin et al. |
| 6,235,893 B1 | 5/2001 | Reibert et al. |
| 6,372,410 B1 | 4/2002 | Ikemoto et al. |
| 6,498,269 B1 | 12/2002 | Merbouh et al. |
| 6,686,325 B2 | 2/2004 | Hoyt et al. |
| 6,831,195 B2 | 12/2004 | Nishimura et al. |
| 6,843,931 B2 | 1/2005 | Sapienza |
| 6,861,009 B1 | 3/2005 | Leist |
| 6,894,135 B2 | 5/2005 | Kiely et al. |
| 6,919,478 B2 | 7/2005 | Kawato et al. |
| 7,125,441 B1 | 10/2006 | Furman et al. |
| 7,314,906 B2 | 1/2008 | Kiely et al. |
| 7,658,861 B2 | 2/2010 | Koefod |
| 7,692,041 B2 | 4/2010 | Kiely |
| 8,153,573 B2 | 4/2012 | Miralles et al. |
| 8,303,721 B2 | 11/2012 | Warkotsch et al. |
| 8,623,943 B2 | 1/2014 | Kiely |
| 8,679,364 B2 | 3/2014 | Pylkkanen |
| 9,096,787 B2 | 8/2015 | Rowley et al. |
| 9,162,959 B2 | 10/2015 | Kiely |
| 9,346,736 B2 | 5/2016 | Donen |
| 9,347,024 B2 | 5/2016 | Smith |
| 2002/0068836 A1 | 6/2002 | Haupfear et al. |
| 2003/0109394 A1 | 6/2003 | Ruhr et al. |
| 2003/0168625 A1 | 9/2003 | Sapienza et al. |
| 2003/0176305 A1 | 9/2003 | Hoyt et al. |
| 2004/0025908 A1 | 2/2004 | Douglas et al. |
| 2004/0028655 A1 | 2/2004 | Nelson et al. |
| 2004/0185562 A1 | 9/2004 | Schroeder et al. |
| 2005/0202981 A1 | 9/2005 | Eveland et al. |
| 2005/0202989 A1 | 9/2005 | Wilson |
| 2005/0230658 A1 | 10/2005 | Koefod |
| 2007/0037727 A1 | 2/2007 | Fiore et al. |
| 2007/0278446 A1 | 12/2007 | Koefod |
| 2008/0033205 A1 | 2/2008 | Kiely et al. |
| 2008/0099716 A1 | 5/2008 | Koefod |
| 2008/0287334 A1 | 11/2008 | Smith et al. |
| 2008/0302737 A1 | 12/2008 | Denkewicz, Jr. et al. |
| 2009/0250653 A1 | 10/2009 | Kiely |
| 2010/0041574 A1 | 2/2010 | Warkotsch et al. |
| 2010/0130774 A1 | 5/2010 | Wan et al. |
| 2010/0191002 A1 | 7/2010 | Kiely |
| 2010/0240566 A1 | 9/2010 | Meine et al. |
| 2010/0242997 A1 | 9/2010 | Smith et al. |
| 2010/0256036 A1 | 10/2010 | Benda et al. |
| 2011/0226288 A1 | 9/2011 | Warkotsch et al. |
| 2011/0232692 A1 | 9/2011 | Zipfel et al. |
| 2011/0263905 A1 | 10/2011 | Purola |
| 2011/0269662 A1 | 11/2011 | Miralles et al. |
| 2011/0312871 A1 | 12/2011 | Miralles et al. |
| 2012/0035356 A1 | 2/2012 | Kiely |
| 2012/0119152 A1 | 5/2012 | Smith |
| 2012/0238005 A1 | 9/2012 | Wieland |
| 2012/0295986 A1 | 11/2012 | Smith |
| 2012/0305832 A1 | 12/2012 | Kiely |
| 2013/0090281 A1 | 4/2013 | Feenstra et al. |
| 2014/0228452 A1 | 8/2014 | Kiely |
| 2014/0275622 A1 | 9/2014 | Donen |
| 2014/0275623 A1 | 9/2014 | Donen |
| 2015/0191549 A1 | 7/2015 | Kiely |
| 2015/0259588 A1 | 9/2015 | Rowley |
| 2015/0376104 A1 | 12/2015 | Kiely |
| 2016/0039735 A1 | 2/2016 | Donen |
| 2016/0102274 A1 | 4/2016 | Smith |
| 2016/0229783 A1 | 8/2016 | Kiely et al. |

FOREIGN PATENT DOCUMENTS

| | | |
|---|---|---|
| CN | 1970488 | 5/2007 |
| DE | 2016686 | 11/1970 |
| DE | 1929968 | 12/1970 |
| DE | 117492 | 1/1976 |
| DE | 3331751 | 3/1984 |
| DE | 3519884 | 1/1986 |
| EP | 0652305 | 5/1995 |
| EP | 0758678 | 2/1997 |
| EP | 0819653 | 1/1998 |
| EP | 1201617 | 5/2002 |
| FR | 2054945 | 6/1971 |
| FR | 2115300 | 8/1972 |
| GB | 866840 | 5/1961 |
| GB | 2405636 | 9/2003 |
| JP | 47048091 | 12/1972 |
| JP | S 50-045744 | 4/1975 |
| JP | S51011030 | 1/1976 |
| JP | 51041578 | 11/1976 |
| JP | 54043840 | 4/1979 |
| JP | S57192270 | 11/1982 |
| JP | S58091174 | 5/1983 |
| JP | S60-50188 | 3/1985 |
| JP | 60108352 | 6/1985 |
| JP | 60112676 | 6/1985 |
| JP | 63248782 | 10/1988 |
| JP | 04214057 | 8/1992 |
| JP | H06306652 | 11/1994 |
| JP | H09104687 | 4/1997 |
| JP | H 09-227900 | 9/1997 |
| JP | 2003306369 | 10/2003 |
| JP | 2004123465 | 4/2004 |
| JP | 2008054806 | 3/2008 |
| KR | 20020066275 | 8/2002 |
| PL | 98149 | 8/1978 |
| RO | 69880 | 4/1981 |
| WO | WO 92/07108 | 4/1992 |
| WO | WO 00/34221 | 6/2000 |
| WO | WO 2004/052958 | 6/2004 |
| WO | WO 2004/052959 | 6/2004 |
| WO | WO 2008/021054 | 2/2008 |
| WO | WO 2009/065143 | 5/2009 |
| WO | WO 2010/086832 | 8/2010 |
| WO | WO 2011/032988 | 3/2011 |
| WO | WO 2011/100344 | 8/2011 |
| WO | WO 2011/138719 | 11/2011 |
| WO | WO 2012/065001 | 5/2012 |
| WO | WO 2012/145688 | 10/2012 |
| WO | WO 2012/145690 | 10/2012 |
| WO | WO 2013/090090 | 6/2013 |
| WO | 2014/085262 | 6/2014 |

(56) References Cited

FOREIGN PATENT DOCUMENTS

| | | |
|---|---|---|
| WO | 2014/159694 | 10/2014 |
| WO | 2016/057497 | 4/2016 |

OTHER PUBLICATIONS

United States Co-pending U.S. Appl. No. 15/135,005 by Donen et al., filed Apr. 21, 2016.
Abbadi et al., New Ca-Sequestering Materials Based on the Oxidation of the Hydrolysis Products of Lactose, Green Chem, 1999, 231-235.
Abd El Kader, J.M. et al., "Corrosion inhibition of mild steel by sodium tungstate in neutral solution. Part 3. Coinhibitors and synergism," British Corrosion Journal, 33, 152-157 (1998) Chern Abstr AN 1998:796697.
Abdallah, M. "Sodium gluconate, triethanolamine and their mixtures as corrosion inhibitors of carbon steel in 3.5% NaC1 solution," Journal of the Electrochemical Society of India, 48, 121-127, (1999) Chern Abst AN 1999:374923.
Allcock, H.R. et al., "Effect of nonstoichiometric reactant ratios on linear condensation polymers," Contemporary Polymer Chemistry, 2nd Edition, Prentice-Hall, New Jersey (1990) Part II, 274-275.
Billmeyer, F.W., Jr., "Molecular weight and molecular-weight distribution," Textbook of Polymer Science, 3rd Edition, Wiley Interscience, New York (1984) 38-47.
Cantrell, C. E., et al., "s-Dicarbonyl Sugars. 5. A Novel Synthesis of a Branched-Chain Cyclitol," J. Org. Chem. (1977) 42(22):3562-3567.
Carter, Andy, "Modifications in the Preparation of Glucaric Acid and Some 4-alkyl-4-azaheptane-1,7-diamines," 1998, Thesis, University of Alabama, Birmingham, AL, p. 18-20.
Chen, L., "Experimental and Theoretical Studies Concerned with Synthetic Acyclic Carbohydrate Based Polyamides," A Dissertation, University of Alabama at Birmingham (1992).
Chen, L. et al., "Synthesis of steroregular head-tail hydroxylated nylons derived from D-glucose," J. Org. Chem. (1996) 61:5847-5851.
Collepardi, M.M.; "Concrete Admixture Handbook: Properties, Science and Technology", 2nd Edition, Ramachandran,V.S. Editor,Noyes Publications, Park Ridge,NJ (1995) p. 286-409.
Cotton, F.A. et al., Advanced Inorganic Chemistry, 1988, p. 341-353, John Wiley and Sons, New York.
CRC Handbook of Chemistry and Physics, edited by Weast et al., 64th Edition, 1983-84, Boca Raton, Florida, p. B-117.
Dorwald, F.Z., Side Reactions in Organic Synthesis. A Guide to Succsesful Synthesis Design, Wiley-VCH Verlag GmbH & Co., Weinheim, Germany (2005) Preface.
Hashimoto et al., "Macromolecular synthesis from caccharic lactones. Ring-opening polyaddition of D-glucaro- and D-mannaro-1,4:6,3-dilactones with alkylenediamines," J. Polym. Sci. Part A: Polym. Chem. (1993) 31:3141-3149.
Hashimoto, K. et al., "Ring-opening polyaddition of D-glucaro-1,4:6,3-dilactone with p-zylylenediamine," Macromol. Chem. Rapid Commun. (1990) 11:393-396.
Haworth et al., "Lactones of mannosaccharic acid, Part I. 2: 5-dimethyl Δ4-manno-saccharo-3: 6-lactone 1-methyl ester, an analogue of ascorbic acid," J. Chem. Soc. London (1944) 56:217-224.
Haworth, W.N. et al., "Some Derivatives of Glucosaccharic Acids," J. Chern. Soc. (1944) 25:65-76.
Kiely et al., "Hydroxylated nylons based on unprotected esterified D-glucaric acid by simple condensation reactions," J. Am. Chem. Soc. (1994) 116(2):571-578.
Kirk-Othmer Encyclopedia of Chemical Technology, 3rd Edition, Wiley, New York, vol. 16, 617-634, "Hydrocarbon Resins" to "Hypnotics, Sedatives, Anticonvulsants", No date.
Korzh, E.N. et al., "Acidity and corrosion activity of brine refrigeratnts based on calcium chloride," Zhurnal Prikladnoi Khimii Journal (Russian) (1981) 54:2404-2407, Chern. Abstr. AN 1982-147045.

Lachman, A., "Dihydroxy-Tartaric Acid," Amer. Chern. Soc. (1921) 43:2091-2097.
Lewis, B.A. et al., Chapter 13, "Galactaric acid and its derivatives," Methods in Carbohydrate Chemistry, R.L. Whistler et al., editors, (1953)II:38-46.
Lin, "Diverse Applications of Carbohydrate Acids in Organic Synthesis," a Dissertation, University of Alabama at Birmingham (1987) p. 48-50, 72-74.
Lowe et al., Soaps and Detergents—The Inorganic Components, J. Am. Oil Chem. Soc., 1978, 55, 32-35.
Mainhardt, H., "N20 Emissions from Adipic Acid and Nitric Acid Production," IPCC Good Practice Guidance and Uncertainty Management in National Greenhouse Gas Inventories (2001).
Marukame, K., S.Fushoku Burnon linkai Shiryo(Nippon Xairyo Gakkai), journal written in Japanese, 173, 1-8, (1993) Chern. Abstr. AN 1993:543767.
Mehletretter, C.L., "D-Giucaric Acid," Methods in Carbohydrate Chemistry, 1963, p. 46-48, vol. II, Academic Press, New York.
Mehltretter, C.L. et al., "Saccharic and Oxalic Acids by the Nitric Acid Oxidation of Dextrose," Agric. and Food Chem. (1953) 1(12):779-783.
Merbough, N. et al., "4-AcNH-tempo-Catalyzed Oxidation of Aldoses to Aldaric Acids Using Chlorine or Bromine as Terminal Oxidants," J. Carbohydr. Chem., 2002, 21:.66-77.
Mor, E. et al., "Steel corrosion inhibition in seawater by calcium organic compounds," Annali deii'University di Ferrara, Sezione 5; Chimica Pura ed Applicata, Journal in French (1971),Chem Abstr AN 1971:414090.
Mor, E. et al., "Zinc gluconate as an inhibitor of the corrosion of mild steel in sea water," Lab Corros. Mar. Met, British Corrosion Journal (1976) 11:199-203 Chem. Abstr. AN 1977:129710.
Mustakas, G.C. et al., "Potassium Acid Saccharate by Nitric Acid Oxidation of Dextrose," Industrial and Engineering Chemistry, Mar. 1954, 427-434.
National Association of Corrosion Engineers (NACE) Standard TM0169-95 as Modified by The Pacific Northwest States, Test Method B, Revision (Apr. 2006).
Ogata, N. et al., "Active polycondensation of diethyl 2,3,4,5-tetrahydroxyadipate with diamines," J. Polym. Sci. Polym. Chem. Ed. (1976) 14:783-792.
Ogata, N. et al., "Copolycondensation of hydroxyl diesters and active diesters with hexamethylenediamine," J. Polym. Sci. Polym. Chem. Ed. (1977) 15:1523-1526.
Ogata, N. et al., "Polycondensation reaction of dimethyl tartrate with hexamethylenediamine in the presence of various matrices," J. Polym. Sci. Polym. Chem. Ed. (1980) 18:939-948.
Ogata, N. et al., "Synthesis of hydrophilic polyamide by active polycondensation," J. Polym. Sci. Polym. Lett. Ed. (1974) 12:355-358.
Ogata, N. et al., "Synthesis of hydrophilic polymide from L-tartarate and diamines by active polycondensation," J. Polym. Sci. Polym. Chem. Ed. (1975) 13:1793-1801.
Ogata, N. et al., "Synthesis of polyamides through active diesters," J. Polym. Sci., Polym. Chem. Ed. (1973) 11:1095-1105.
Ogata, N. et al., "Synthesis of polyesters from active diesters," J. Polym. Sci. Chem. Ed. (1973) 11:2537-2545.
Ogata, N., "New polycondensation systems," Polym. Prepr. (1976) 17:151-156.
Pamuk et al. "The preparation of D-glucaric acid by oxidation of molasses in packed beds" Journal of Chemical Technology and Biotechnology (2001) 76:186-190.
Roper, H., "Selection oxidation of D-glucose: chiral intermediates for industrial utilization," Starch/Starke (1990) 42(9):342-349.
Stanek, J. et al., "Monosaccharide dicarboxylic acids," The Monosaccharides, Academic Press, New York and London (1963) Chapter XXXII, p. 741-752.
Styron, S.D. et al., "MM3(96) conformational analysis of D-glucaramide and x-ray crystal structures of three D-glucaric acid derivatives—models for synthetic poly(alkylene D-glucaramides," J. Carb. Chem. (2002) 21(1&2):27-51.
Sukhotin,A.M. et al., "Corrosion inhibitor for steel in calcium chloride solutions," Zashchita Mettalov, Journal in Russion (1982) 18:268-70, Chem Ab 1982:476671.

(56) References Cited

OTHER PUBLICATIONS

Van Duin et al., Studies on borate esters. Part 8. Interactions of cations with oxyacid anion-bridged esters of D-glucarate in alkaline media, J. Chem. Soc. Dalton Trans., 1987, 8, 2051-2057.
Van Duin et al., Synergic Coordination of Calcium in Borate-Polyhydroxycarboxylate Systems, Carb. Res., 1987, 162, 65-78.
Van Duin, M. et al., "Studies on borate esters. Part 5. The system glucarate borate calcium (II) as studied by 1H, 11B, and 13C nuclear magnetic resonance spectroscopy," J. Chem. Soc. (1987) 2(4):473-478.
Werpy, T. et al., Top Value Added Chemicals from Biomass, Voil-Results of Screening for Potential, www.osti.gov/bridge, U.S. Dept. of Energy, Oak Ridge, TN (2004) 76 pages.
Wilham et al., Organic Acids as Builders in Linear Alkylbenzene Sulfonate Detergent Formulations, J. Am. Oil Chem. Soc., 1971, 48(11), 682-683.
Wisconsin Biorefiners Development Initiative and references therein, Biorefining Processes-Fermentation of 6-Carbon Sugars and Starchs, www.wisbiorefine.org/proc/ferments.pdr (Feb. 5, 2007).
Wrubl, C. et al., "Zinc gluconate as an inhibitor of the corrosion of copper and zinc in seawater," 1st Corros. Mar Met, British Corrosion Journal (1983) 18:142-147, Chem. Abstr. AN 1984:11228.
Yahiro et al., "Efficient acid production from raw corn starch," J. Fermentation Bioengineering (1997) 84(4):375-377.
International Preliminary Report on Patentability for Application No. PCT/US2007/017493 dated Feb. 10, 2009.
International Preliminary Report on Patentability for Application No. PCT/US2008/083831 dated May 18, 2010 (8 pages).
International Preliminary Report on Patentability for Application No. PCT/US2011/060264 dated May 23, 2013 (8 pages).
International Search Report and Written Opinion for Application No. PCT/US2012/034538 dated Jul. 10, 2012 (11 pages).
International Search Report and Written Opinion for Application No. PCT/US2012/034542 dated Jul. 10, 2012 (10 pages).
International Search Report for Application No. PCT/US2003/039733 dated May 13, 2004 (2 pages).
International Search Report for Application No. PCT/US2007/017493 dated Feb. 12, 2008.
International Search Report for Application No. PCT/US2011/060264 dated Feb. 10, 2012.
International Search Report and Written Opinion for Application No. PCT/US2013/071520 dated Feb. 5, 2014 (12 pages).
International Search Report and Written Opinion for Application No. PCT/US2014/024785 dated Jul. 7, 2014 (13 pages).
International Search Report and Written Opinion for Application No. PCT/US2015/054218 dated Jan. 14, 2016 (13 pages).
United States Patent Office Action for U.S. Appl. No. 11/890,760 dated Apr. 16, 2009 (7 pages).
United States Patent Office Action for U.S. Appl. No. 11/890,760 dated Jul. 25, 2008 (8 pages).
United States Patent Office Action for U.S. Appl. No. 12/272,732 dated Apr. 26, 2011.
United States Patent Office Action for U.S. Appl. No. 12/272,732 dated Aug. 24, 2010.
United States Patent Office Action for U.S. Appl. No. 12/272,732 dated Dec. 9, 2011.
United States Patent Office Action for U.S. Appl. No. 12/272,732 dated Jul. 6, 2012 (12 pages).
United States Patent Notice of Allowance for U.S. Appl. No. 12/272,732 dated Aug. 9, 2013 (9 pages).
United States Patent Office Action for U.S. Appl. No. 12/442,135 dated May 16, 2012 (7 pages).
United States Patent Office Action for U.S. Appl. No. 12/442,135 dated Oct. 26, 2011 (7 pages).
United States Patent Office Action for U.S. Appl. No. 12/753,721 dated Dec. 12, 2011 (7 pages).
United States Patent Office Action for U.S. Appl. No. 12/753,721 dated May 9, 2013 (8 pages).
United States Patent Office Notice of Allowance for U.S. Appl. No. 11/890,760 dated Jan. 8, 2010 (6 pages).
United States Patent Office Notice of Allowance for U.S. Appl. No. 12/753,721 dated Aug. 3, 2012 (5 pages).
United States Patent Office Action for U.S. Appl. No. 13/586,953 dated Jul. 1, 2013 (7 pages).
United States Patent Office Action for U.S. Appl. No. 13/586,953 dated Jan. 27, 2014 (7 pages).
United States Patent Office Notice of Allowance for U.S. Appl. No. 13/586,953 dated Aug. 7, 2014 (6 pages).
United States Patent Office Action for U.S. Appl. No. 13/452,560 dated Dec. 4, 2013 (11 pages).
United States Patent Office Action for U.S. Appl. No. 13/452,560 dated Aug. 19, 2014 (10 pages).
United States Patent Office Action for U.S. Appl. No. 13/452,560 dated Jun. 18, 2015 (10 pages).
United States Patent Office Notice of Allowance for U.S. Appl. No. 13/452,560 dated Jan. 20, 2016 (10 pages).
United States Patent Office Action for U.S. Appl. No. 13/452,578 dated Sep. 23, 2014 (12 pages).
United States Patent Office Action for U.S. Appl. No. 13/452,578 dated Jul. 16, 2015 (16 pages).
United States Patent Office Action for U.S. Appl. No. 14/150,633 dated Sep. 25, 2014 (12 pages).
United States Patent Office Notice of Allowance for U.S. Appl. No. 14/150,633 dated Jun. 8, 2015 (9 pages).
United States Patent Office Action for U.S. Appl. No. 13/294,085 dated Oct. 3, 2014 (18 pages).
United States Patent Office Action for U.S. Appl. No. 13/294,085 dated Apr. 1, 2015 (15 pages).
United States Patent Office Action for U.S. Appl. No. 13/294,085 dated Aug. 27, 2015 (6 pages).
United States Patent Office Action for U.S. Appl. No. 14/089,054 dated Aug. 15, 2014 (16 pages).
United States Patent Office Notice of Allowance for U.S. Appl. No. 14/089,054 dated Mar. 2, 2015 (7 pages).
United States Patent Office Action for U.S. Appl. No. 14/107,297 dated Mar. 11, 2015 (4 pages).
United States Patent Office Action for U.S. Appl. No. 14/107,297 dated Jun. 19, 2015 (8 pages).
United States Patent Office Notice of Allowance for U.S. Appl. No. 14/107,297 dated Dec. 16, 2015.
United States Patent Office Action for U.S. Appl. No. 14/205,627 dated Aug. 27, 2014 (25 pages).
United States Patent Office Action for U.S. Appl. No. 14/205,627 dated May 15, 2015 (28 pages).
United States Patent Office Notice of Allowance for U.S. Appl. No. 14/205,627 dated Jan. 21, 2016 (10 pages).
United States Patent Office Action for U.S. Appl. No. 14/205,832 dated Aug. 27, 2014 (21 pages).
United States Patent Office Action for U.S. Appl. No. 14/205,832 dated May 12, 2015 (27 pages).
United States Patent Office Action for U.S. Appl. No. 14/205,832 dated Dec. 31, 2015 (18 pages).
United States Patent Office Action for U.S. Appl. No. 14/206,796 dated Nov. 4, 2014 (35 pages).
United States Patent Office Notice of Allowance for U.S. Appl. No. 14/206,796 dated Jul. 17, 2015 (8 pages).
United States Patent Office Action for U.S. Appl. No. 12/422,135 dated Dec. 17, 2014 (8 pages).
United States Patent Office Action for U.S. Appl. No. 14/727,712 dated Jun. 26, 2015 (14 pages).
United States Patent Office Action for U.S. Appl. No. 14/579,938 dated Jan. 20, 2016 (5 pages).
United States Patent Office Action for U.S. Appl. No. 14/849,991 dated Feb. 11, 2016 (7 pages).
United States Patent Office Notice of Allowance for U.S. Appl. No. 14/727,712 dated Feb. 19, 2016 (9 pages).
U.S. Appl. No. 15/196,970, filed Jun. 29, 2016, Smith et al.
United States Patent Office Notice of Allowance for U.S. Appl. No. 14/727,712 dated Jun. 1, 2016 (7 pages).
United States Patent Office Action for U.S. Appl. No. 13/452,578 dated Jul. 14, 2016 (15 pages).

(56) References Cited

OTHER PUBLICATIONS

United States Patent Office Action for U.S. Appl. No. 14/887,635 dated Jul. 28, 2016 (28 pages).
United States Patent Office Action for U.S. Appl. No. 14/205,832 dated Sep. 30, 2016 (9 pages).
United States Patent Office Action for U.S. Appl. No. 14/849,991 dated Sep. 12, 2016 (7 pages).
United States Patent Office Notice of Allowance for U.S. Appl. No. 14/727,712 dated Sep. 16, 2016 (7 pages).

HYDROXYPOLYAMIDE GEL FORMING AGENTS

CROSS-REFERENCE TO RELATED APPLICATIONS

This application claims the benefits of U.S. Provisional Application No. 61/003,444, filed Nov. 15, 2007, the disclosure of which is hereby incorporated by reference in its entirety including all figures, tables and drawings.

STATEMENT REGARDING FEDERALLY SPONSORED RESEARCH OR DEVELOPMENT

This invention was made with Government support under Grant Nos. 2004-34463-14477; 2005-34463-15561; and 2006-34463-16886 awarded by the USDA CREES. The Government has certain rights in the invention.

REFERENCE TO SEQUENCE LISTING, A TABLE, OR A COMPUTER PROGRAM LISTING COMPACT DISC APPENDIX

Not applicable

BACKGROUND OF THE INVENTION

Gel forming agents are materials that, when in contact with a liquid or fluid substance, cause that liquid or fluid substance to become a gel. Applications of gel forming materials include absorbing urine in diapers (particularly, disposable diapers) (Buchholz, 1994; Buchholz, 1996) gel formation with other bodily fluids in health care products, use in a variety of personal hygiene products, use in fluid absorption in medical procedures, use in time release drug delivery (Jeong, 1997), use in cell culturing (von Recum, 1998; Kisiday, 2002) and tissue regeneration (growth) (Lee, 2001), and use in agriculture techniques including water (Hüttermann, 1999), fertilizer (Karadağ, 2000), and pesticide (Rudziniski, 2002) controlled release. New gel forming agents are of interest as commercial entities if they display improved or different gel forming properties from those currently available.

All patents, patent applications, provisional patent applications and publications referred to or cited herein, are incorporated by reference in their entirety to the extent they are not inconsistent with the teachings of the specification.

BRIEF SUMMARY OF THE INVENTION

Hydroxypolyamides and hydroxypolyamide products are described and claimed for use as gel forming agents. These hydroxypolyamides or hydroxypolyamide products are combined with aqueous or non-aqueous liquids to produce gels. Known methods can be used to prepare hydroxypolyamides which can serve as gel forming agents. Hydroxypolyamide products with superior gel forming ability are prepared by a modified polymerization method that includes a basification step utilizing a base stronger than a tertiary amine. Gel forming properties of some hydroxypolyamides were improved in the presence of dissolved salts in the liquid medium.

DETAILED DESCRIPTION OF THE INVENTION

The invention involves the preparation and use of hydroxypolyamides and hydroxypolyamide products as gel forming agents. An improved basification step is disclosed for the method of preparing the hydroxypolyamide products. Use of these hydroxypolyamides and hydroxypolyamide products as significant liquid absorbers to make gels, and particularly gel formation with water or aqueous solutions, including bodily fluids such as urine, to produce hydrogels is also disclosed.

Gel forming agents are defined here as chemical substances which are capable of immobilizing a liquid/or fluid (labeled hereafter as liquid) into a deformable, semi-solid material known as a gel. Gels were further classified as strong gels or weak gels. A strong gel retained its shape and position in the gel container when that container was inverted. Gel forming agents were classified as very good, good or moderate depending upon the amount of material required to make a strong gel, that is, very good gel forming agents required the least amount of gel forming agent to form a strong gel.

The subject gel forming materials exhibit good natural degradability in soil (Jahns, 2006) and aqueous systems, are derived in part from renewable carbohydrates, and offer a range of applications based upon the structural diversity of materials available by the technology employed. These materials offer improvements in some gel forming applications currently in use, they offer improvements in some gel forming applications where the current polymeric gel forming agents undergo no to very little natural degradation in soil and water, and they offer improvements in some gel forming applications where the current degradation products in soil and water are toxic to plants and/or animals.

A structural variety of gel forming agents have been produced by the technology described. These agents degrade relatively rapidly in soil and/or water and can be considered as environmentally compatible materials (Jahns, 2006). The examples reported include: a) preparation of hydroxypolyamides derived in part from carbohydrate diacids and b) the use of hydroxypolyamides as gel forming agents.

Commercial markets for gel forming agents include a very large market for super absorbent polymers (SAPs) (Buchholz, 1994; Buchholz, 1996) that are used in disposable diapers and other human fluid adsorbing applications, and water/fertilizer delivery systems for agricultural and horticultural applications (Hüttermann, 1999; Karadağ, 2000; Rudziniski, 2002).

The preparation of a variety of hydroxypolyamides (U.S. Pat. No. 6,894,135 B2; Kiely, 1994; and U.S. Pat. No. 4,833,230), by polymerization of polyacids (carboxylic acids with two or more carboxylic acid functions) and/or carboxyl group activated polyacids with polyamines (amines with two or more amine functions), where some of the polyacid monomers and/or some of the polyamine monomers bear one or more pendant hydroxyl groups is described.

The hydroxypolyamides from the reported polymerization methods (U.S. Pat. No. 6,894,135 B2; Kiely, 1994; and U.S. Pat. No. 4,833,230) and the hydroxypolyamide products reported here were evaluated as gelling agents with both aqueous and organic based liquids. The liquids were single substance liquids or liquids with dissolved solid and/or liquid substances.

In general, the procedures employed to make the polymer products for gel forming applications can be derived by condensing (combining) a broad spectrum of amines and organic acids that include polyamine/polycarboxylic acid combinations. More specifically amines used as monomers in the polymerizations are of the following types: alkylenepolyamines; alkenylenepolyamines; alkynylenepolyamines;

alkylarylpolyamines; alkenylarylpolyamines; alkynylarylpolyamines; carbocyclic polyamines; heterocyclic polyamines; any of the above polyamines substituted with one or more alkyl, alkenyl, or alkynyl groups, substituted alkyl, alkenyl, or alkynyl groups, aryl groups or substituted aryl groups, other groups, atoms other than hydrogen; any of the above polyamines with one or more hetero atoms such as, but not limited to, N, O, P, or S in place of one or more carbon atoms the above polyamines substituted with one or more hydroxyl groups or other pendant groups that include, but are not limited to ester, ether, ketone, thiol, thioether, nitro, nitrile, cyano, and other common groups.

More specifically carboxylic acids used as monomers in the polymerizations are of the following types: aliphatic polyacids, carbocyclic polyacids, heterocyclic polyacids, arylalkyl polyacids, the above polyacids with a substituent or substituents that include alkyl, alkenyl, or alkynyl groups, substituted alkyl, alkenyl, or alkynyl groups, aryl groups and/or substituted aryl groups, other groups, atoms other than hydrogen; the above polyacids with one or more hetero atoms such as, but not limited to, N, O, P, or S in place of one or more carbon atoms; the above polyacids substituted with one or more hydroxyl groups or other pendant groups that include, but are not limited to ester, ether, ketone, thiol, thioether, nitro, nitrile, cyano, and other common groups.

Different hydroxypolyamide and hydroxypolyamide products with different properties, including different gelling properties, are derived from one or more polyamines in combination with one or more polyacids.

Superior gel forming hydroxypolyamide products described here were formed unexpectedly using a modification of a recently reported method for preparation of hydroxypolyamides (U.S. Pat. No. 6,894,135 B2), as compared to older methods of preparation (Kiely, 1994; and U.S. Pat. No. 4,833,230). It was first reported that hydroxypolyamides could be formed by reaction between bis primary amines and esterified aldaric acids in a polar solvent (U.S. Pat. No. 4,833,230). A limitation of this method of polyamide preparation is the difficulty in achieving stoichiometric equivalency between the acid monomer(s) and the amine monomer(s), an important requirement for making high molecular weight condensation polymers. A more recent report describes a procedure to achieve stoichiometric equivalency between the two monomers by first making the corresponding amine:acid salt directly from the carbohydrate acid and the diamine or polyamine (U.S. Pat. No. 6,894,135 B2). This product is then treated with an inorganic acid ($H^+ X^-$) in alcohol to give the esterified acid:ammonium/$X^-$ salt. For example, when the salt is formed from an aldaric acid and an alkylenediamine, the product from the inorganic acid ($H^+ X^-$) in alcohol treatment is the esterified aldaric acid:alkylenediammonium di $X^-$ salts. This mixture is then basified to give the diamine which undergoes condensation with the esterified aldaric acid. Previously, basification was carried out using only a tertiary amine base (U.S. Pat. No. 6,8984,135 B2); however, a modified basification process was developed employing a combination of a relatively strong base (e.g., alkoxide) and a weaker tertiary amine base for deprotonation of the ammonium units.

For the basification step, the stronger base (e.g., alkoxide) is used to deprotonate the bulk of the ammonium salt(s) (>90 mol %) to the free amine form(s). Also included in the basifying medium is some tertiary amine (U.S. Pat. No. 6,894,135 B2). Use of these bases produces hydroxypolyamides of higher molecular weight than those employing only a tertiary amine as the base or from the direct condensation of a polyamine with an esterified hydroxypolyacid.

The hydroxypolyamides produced in this way are different in some way, in addition to being of higher molecular weight, than the hydroxypolyamides prepared according to previous methods (Kiely, 1994; U.S. Pat. No. 4,833,230; U.S. Pat. No. 6,894,135 B2, U.S. Pat. No. 5,434,233, and Morton, 2000), despite originating from the same hydroxypolyacid(s)/polyamine(s), and as such are labeled as hydroxypolyamide products. A second noted difference is that the hydroxypolyamide products contained a small amount (<10%) of inorganic salt (sodium chloride), a result of the method of preparation of the hydroxypolayamide products that included deprotonation of derived ammonium salts (chlorides) with a base stronger than a tertiary amine, e.g., sodium methoxide. Their difference(s) manifests itself in the unexpected result that in general, hydroxypolyamide products derived from the disalt/modified basification method had superior gel forming properties compared to the corresponding hydroxypolyamides formed from the previous methods.

In the method of polyamide preparation previously described (U.S. Pat. No. 6,894,135 B2), both pre-polymers (pre-hydroxypolyamides) and post-polymers (post-hydroxypolyamides) are described, the post-polymers being made by polymerization of the pre-polymers, and being of higher molecular weight. As indicated in Section 0014, the superior gel forming ability of the hydroxypolyamide products compared to hydroxypolyamides prepared by previously reported methods is seen as originating from a difference between these materials that is not simply attributable to the higher molecular weight of the hydroxypolyamide products. That is supported by the observation that yet higher molecular weight post-hydroxypolyamides exhibit inferior gel forming ability compared to the hydroxypolyamide products described. However, in general, the gel forming performance of post-polyamides was improved in the presence of added inorganic salts and/or organic salts. Hydrogel forming materials such as the polyacrylic acid based SAPs used in disposable diapers, absorb water much more efficiently then they absorb urine or other aqueous solutions. That is, it takes considerably more of the polyacrylic acid based polymer to absorb urine or other aqueous solutions than to absorb the same volume of water. The performance of these SAPs is also severely diminished in aqueous solutions that are basic buffered solutions (e.g., pH 10) and acidic buffered solutions (e.g., pH 4). The performance of hydroxypolyamide gel forming materials of the subject invention is comparable when water, aqueous salt solutions, aqueous acid solutions, aqueous base solutions, aqueous acid buffer solutions, or aqueous base buffer solutions are used in hydrogel formation. In general the hydrogel forming performance of SAPs is severely compromised in the presence of dissolved salts, whereas the hydrogel forming performance of the hydroxypolyamide or hydroxypolyamide product gel forming materials is improved, unchanged, or at worst, minimally reduced under the same conditions. Hydroxypolyamide or hydroxypolyamide product gel forming materials can be effective over a broad pH range and in the presence of dissolved substances in the aqueous medium giving them properties that offer practical and improved hydrogel applications.

It was determined that some hydroxypolyamides or hydroxypolyamide products formed gels by being first dissolved in a small amount of organic solvent and then combined with water or aqueous solutions. Other hydrogel forming agents performed by direct dissolution in water or aqueous solutions. Other gels formed directly in non-aqueous liquids.

It was determined that some hydroxypolyamides or hydroxypolyamide products that were readily soluble in water or aqueous solutions formed gels upon rendering the resultant aqueous solutions basic. Gels could be formed from organic liquids, aqueous/organic liquid solutions, and aqueous solutions with a single or multiple dissolved substances which were salts or non-salts.

The hydroxypolyamides and hydroxypolyamide products of the subject invention form gels when in contact with a liquid(s). The liquid(s) can be aqueous (water) and/or non-aqueous (organic) liquids. The liquids can be aqueous or non-aqueous single liquids. The liquids can be aqueous and/or non-aqueous multiple liquids. The liquids can be combined aqueous and non-aqueous liquids.

The liquids can be aqueous and/or non-aqueous single liquids with one or more dissolved and/or undissolved materials, solids and/or liquids. The liquids can be aqueous and/or non-aqueous multiple liquids with one or more dissolved or undissolved materials, solids and/or liquids. The dissolved or undissolved materials can be mammalian bodily fluids that include, but are not limited to, urine, blood, mucous or other bodily fluids. The dissolved or undissolved materials can be agents such as pharmaceutical agents that are organic materials, non-organic materials, or organic:non-organic combined materials or mixtures thereof that when applied to a living system, can bring about some change(s), particularly beneficial change(s), to that appropriate living system. The dissolved or undissolved materials can be agents such as fertilizers or fertilizer components, pesticides or pesticide components, herbicides or herbicide components, nutrients, trace metals or other materials, organic materials, non-organic materials, or organic/non-organic combined materials or mixtures thereof that when applied can bring about some chemical, physical, or biochemical change in the surrounding environment (soil, ground surfaces, ground sub-surface, water bodies including, but not limited to, streams, rivers, ponds, lakes and seawater containing waters) where they are applied, and particularly some beneficial change(s) to the living systems found in that environment. The living system(s) can be from the plant kingdom and/or animal kingdom.

Gel forming properties are from hydroxypolyamides formed from the reported methods of preparation (U.S. Pat. No. 6,894,135 B2; Kiely, 1994; U.S. Pat. No. 5,434,233; Morton, 2000; Smith, 2006; and Smith, 2007) or hydroxypolyamide products described here. Moderate to very good hydrogel forming properties are found with pre-hydroxypolyamides formed from reported methods of preparation (U.S. Pat. No. 6,894,135 B2 and Kiely, 1994). Very good hydrogel forming properties are found with hydroxypolyamide products formed by a modification of a recent method of preparation (U.S. Pat. No. 6,894,135 B2), wherein a base stronger than a tertiary amine, such as triethylamine, is used in the ammonium deprotonation step in order to initiate the polymerization (Smith, 2006 and Smith, 2007). A preferred base that is a stronger base than a tertiary amine is an alkoxide base. Preferred cation portions of the alkoxide base are metal cations. Cation portions of the alkoxide base are not limited however to metal cations but can be organic cations. The metal cations include, but are not limited to, sodium, potassium, lithium, beryllium, magnesium, and calcium cation.

Hydrogel forming properties of post-hydroxypolyamides (U.S. Pat. No. 6,894,135 B2) can be improved in the presence of added salts that include inorganic salts and/or organic salts and/or salts composed of inorganic and organic structural components. Inorganic salts that improve the hydrogel forming characteristics of the post-hydroxypolyamides include, but are not limited to, lithium, sodium, potassium, magnesium, and calcium salts. Organic salts that improve the hydrogel forming characteristics of the post-hydroxypolyamides include, but are not limited to, alkylenediammonium di $X^-$ salts, wherein di $X^-$ is two common mono-anions such as two chlorides, or one common dianion such as sulfate, salts derived from carboxylic, di- and polycarboxylic acids.

Hydroxypolyamides, hydroxypolyamide products, and post-hydroxypolyamides disclosed that are useful as gelling agents for aqueous and organic liquids include hydroxypolyamides, hydroxypolyamide products, and post-hydroxypolyamides derived from a single polyacid with one or more pendant hydroxyl groups and one polyamine, for example, hexamethylenediamine and D-glucaric acid.

Further, hydroxypolyamides, hydroxypolyamide products, and post-hydroxypolyamides derived from one polyacid having one or more pendant hydroxyl groups and two or more polyamines are useful according to the subject invention. Examples include hydroxypolyamides, hydroxypolyamide products, and post-hydroxypolyamides derived from D-glucaric acid and ethyenediamine/hexamethylenediamine in polyamine ratios of 1:5, 1:4, 1:3, and 1:2; D-glucaric acid and tetramethylenediamine/hexamethylenediamine in polyamine ratios of 1:4, 1:3, 1:2 and 1:1; D-glucaric acid and tetramethylenediamine/octamethylenediamine in a polyamine ratio of 1:1; D-glucaric acid and tetramethylenediamine/dodecamethylenediamine in a polyamine ratio of 4:1.

Hydroxypolyamides, hydroxypolyamide products, and post-hydroxypolyamides derived from two or more polyacids having one or more pendant hydroxyl groups and one polyamine are also useful as gel forming agents and include, but are not limited to, hydroxypolyamides, hydroxypolyamide products, and post-hydroxypolyamides derived from xylaric acid/D-glucaric acid and hexamethylenediamine in a polyacid ratio of 1:6.

Also useful according to the subject invention are hydroxypolyamides, hydroxypolyamide products, and post-hydroxypolyamides derived from two or more polyacids having one or more pendant hydroxyl groups and two or more polyamines. For example, hydroxypolyamides, hydroxypolyamide products, and post-hydroxypolyamides derived from xylaric acid/D-glucaric acid and tetramethylene/hexamethylenediamine in a polyacid and a polyamine ratio of 1:4.

Polymers useful according to the subject invention include hydroxypolyamides, hydroxypolyamide products, and post-hydroxypolyamides derived from one or more polyacids having one or more pendant hydroxyl groups and one polyamine with one or more of the methylene units in the diamine or polyamine being replaced by a hetero atom(s) such as N, O, P, or S.

Also useful as gel forming agents are hydroxypolyamides, hydroxypolyamide products, and post-hydroxypolyamides derived from one polyacid having one or more pendant hydroxyl groups and two or more polyamines with one or more of the methylene units in the polyamine being replaced by a hetero atom(s) such as N, O, P, or S. For example, hydroxypolyamides, hydroxypolyamide products, and post-hydroxypolyamides derived from D-glucaric acid and 4'-aza-4'-methylheptamethylenediamine/hexamethylenediamine in polyamine ratios of 1:4, 1:3, 1:2, 2:3, and 1:1; D-glucaric acid and 3',6'-dioxaoctamethylenediamine/hexamethylenediamine in a polyamine ratio of 1:2.

Hydroxypolyamides, hydroxypolyamide products, and post-hydroxypolyamides derived from two or more polyacids having one or more pendant hydroxyl groups and two or more polyamines with one or more of the methylene units in the polyamine being replaced by a hetero atom(s) such as N, O, P, or S.

Hydroxypolyamides, hydroxypolyamide products, and post-hydroxypolyamides derived from one or more polyacids having one or more pendant hydroxyl groups and one or more polyamines containing one or more pendant groups on the carbon or hetero atom(s) in the polyamine, including, but not limited to, hydroxypolyamides, hydroxypolyamide products, and post-hydroxypolyamides derived from D-glucaric acid and 2-methylpentamethylenediamine/hexamethylenediamine in a polyamine ratio of 1:1; D-glucaric acid and L-lysine/hexamethylenediamine in a polyamine ratio of 1:3 are also useful according to the subject invention.

Branching hydroxypolyamides, hydroxypolyamide products, and post-hydroxypolyamides derived from one or more than one polyacid with at least one pendant hydroxyl group, and more than one polyamine where at least one polyamine monomer contains more than two reactive amine groups are also useful according to the subject invention. For example, hydroxypolyamides, hydroxypolyamide products, and post-hydroxypolyamides derived from D-glucaric acid and tris (2-aminoethyl)amine/hexamethylenediamine in a polyamine ratio of 1:4.

Charged hydroxypolyamides, hydroxypolyamide products, and post-hydroxypolyamides derived from one polyacid having one or more pendant hydroxyl groups and two or more polyamines are useful according to the subject invention. Examples are hydrochloride salts of hydroxypolyamides, hydroxypolyamide products, and post-hydroxypolyamides derived from D-glucaric acid and 4'-aza-4'-methylheptamethylenediamine/hexamethylenediamine in polyamine ratios of 1:4, 1:3 and 1:2; and sodium salts of hydroxypolyamides, hydroxypolyamide products, and post-hydroxypolyamides derived from D-glucaric acid and L-lysine/hexamethylenediamine in a polyamine ratio of 1:3.

Charged hydroxypolyamides, hydroxypolyamide products, and post-hydroxypolyamides derived from one or more polyacids and one or more polyamines that form gels when the charge is chemically altered. For example, solutions of hydrochloride salts of hydroxypolyamides, hydroxypolyamide products, and post-hydroxypolyamides derived from D-glucaric acid and 4'-aza-4'-methylheptamethylenediamine/hexamethylenediamine in polyamine ratios of 2:3 and 1:2 treated with base.

The above hydroxypolyamides, hydroxypolyamide products, and post-hydroxypolyamides in combination with dissolved or undissolved materials, that include inorganic materials, organic materials, biological materials or combinations of said materials can be used as gel forming agents.

Further, hydroxypolyamides, hydroxypolyamide products, and post-hydroxypolyamides in combination with salts that include, but are not limited to, cation anion combinations consisting of one or more cations from the group lithium, sodium, potassium, calcium, magnesium, ammonium, and silver and one or more anions from the group fluoride, chloride, bromide, iodide, nitrate, sulfate, phosphate, glucarate, and acetate can be used as gel forming agents. For example, the above hydroxypolyamides, hydroxypolyamide products, and post-hydroxypolyamides in combination with sodium chloride.

Gel forming agents for aqueous solutions that contain urine include the above hydroxypolyamides, hydroxypolyamide products, and post-hydroxypolyamides.

Gel forming agents for aqueous solutions that contain components of common fertilizers, such as monopotassium phosphate and potassium nitrate, include the above hydroxypolyamides, hydroxypolyamide products, and post-hydroxypolyamides.

The following examples are offered to further illustrate but not limit both the compositions and the methods of the present invention.

Experimental Procedures for Synthesis of and Gel Preparation with Hydroxypolyamides, Hydroxypolyamide Products, and Post-Hydroxypolyamides.

General Methods.

Monopotassium D-glucarate and sodium methoxide solution (NaOMe) (0.5 M in methanol) were commercial products. Methyl D-glucarate 1,4-lactone was prepared as previously described (Kiely, 1994). Some carbohydrate diacids and diamines or polyamines were prepared as needed. Other commercial chemicals and solvents were used without further purification. Solutions were concentrated in vacuo (15-20 mbar) using a rotary evaporator and water bath at 30° C. pH was estimated using pHydrion paper produced by Micro Essential Laboratory (Brooklyn, N.Y., USA).

Gel Preparations and Classifications.

Gel formations were carried out in 4 mL screw top vials. A mixture was classified as a gel if it remained stable upon inversion of the vial. Gels were further classified as very good, good and moderate depending upon the amount of material required to make a gel. Very good gels were formed using approximately 0.75% (by weight) or less of gel forming material compared to the liquid amount, approximately 99.25% (by volume) or more. Good gels were formed using approximately 0.8% to 1.5% (by weight) of gel forming material compared to the liquid amount, approximately 99.2% to 98.5% (by volume). Moderate gels were formed using approximately 1.6% to 5.0% (by weight) of gel forming material compared to the liquid amount, approximately 98.4% to 95.0% (by volume).

Representative Example Synthesis of Hydroxypolyamide Products from Alkylenediammonium Aldarates or Derivatives Thereof. Step 1—Preparation of an alkylenediammonium aldarate or alkylenediammonium aldarate with one or more methylene units of the alkylenediammonium unit replaced by one or more hetero atoms. Step 2—Esterification and basification of the salt product from Step 1.

Example 1

Poly(hexamethylene D-glucaramide) Hydroxypolyamide Product

Step 1. Hexamethylenediammonium D-Glucarate. Acid form cation exchange resin (70 mL, 0.14 mol, Dowex 50WX8-100, 2.1 meq/mL) was washed with deionized water (3×150 mL). Monopotassium D-glucarate (20.00 g, 80.57 mmol) was added to a slurry of the washed resin in water (100 mL), and the mixture was agitated for 10 min. The resin was removed by filtration and washed with water (3×20 mL). Hexamethylenediamine (9.77 g, 84.1 mmol) was added to the combined filtrate and washings, and the resulting solution was stirred for 3 h then concentrated to a viscous syrup. Methanol (200 mL) was added to the syrup, and the mixture was stirred until all of the oil precipitated as a fine, white solid (18 h). The precipitate was isolated by filtration, washed with methanol (3×20 mL) and dried at reduced pressure for 18 h to give hexamethylenediammonium D-glucarate (24.02 g, 73.60 mmol, 91.33%).

Step 2. Poly(hexamethylene D-glucaramide) Hydroxypolyamide Product. Acetyl chloride (2.0 mL, 28 mmol) was added dropwise to methanol (45 mL) at 0° C., and the solution was allowed to warm to room temperature (10 min) before hexamethylenediammonium D-glucarate (2.29 g, 7.02 mmol) was added. The solution was stirred for 3 h at room temperature then concentrated to a solid. After drying at reduced pressure for 18 h, the solid was re-dissolved in methanol (20 mL). Sodium methoxide solution (26 mL, 13 mmol) and triethylamine (Et$_3$N) (0.49 mL, 3.5 mmol) were added to the methanol solution, and a precipitate was observed within 30 min. After stirring the mixture at room temperature for 24 h, the precipitate was isolated by filtration, washed with methanol (3×10 mL), and dried at reduced pressure for 18 h to give poly(hexamethylene D-glucaramide) polyhydroxypolyamide product (1.52 g, 5.24 mmol, 74.6%).

Representative Synthesis of a Poly($C_x$:$C_y$ D-glucaramide) Hydroxypolyamide Product. $C_x$ and $C_y$ represent a range of acyclic or cyclic alkylene units or acyclic alkylene units or alkylated or otherwise substituted alkylene units, and/or alkylene units replaced by one or more hetero atoms (e.g., N, O, P, or S, etc.), and/or arylalkyl units with pendant unsubstituted and/or alkylated or otherwise substituted methylene units, and/or a carbocylic or heterocyclic units of varying structure with pendant unsubstituted and/or alkylated or otherwise substituted methylene units. The methylene units, substituted or otherwise unsubstituted, are each connected to a nitrogen atom of an amide unit(s) in the polyamide(s).

Example 2

Poly(ethylene:hexamethylene D-glucaramide) (1:4) Hydroxypolyamide Product

Step 1. Hexamethylenediammonium D-Glucarate and Ethylenediammonium D-Glucarate. See method for Step 1, Example 1.

Step 2. Poly(ethylene:hexamethylene D-glucaramide) (1:4)Hydroxypolyamide Product. Acetyl chloride (1.0 mL, 14 mmol) was added dropwise to methanol (25 mL) at 0° C. The solution was allowed to warm to room temperature (10 min) before ethylenediammonium D-glucarate (0.19 g, 0.70 mmol) and hexamethylenediammonium D-glucarate (0.92 g, 2.8 mmol) were added. The solution was stirred for 3 h at room temperature then concentrated to a solid. After drying at reduced pressure for 18 h, the solid was re-dissolved in methanol (10 mL). Sodium methoxide solution (13 mL, 6.5 mmol) and triethylamine (0.25 mL, 1.8 mmol) were added to the methanol solution, and a precipitate was observed within 45 min. After stirring the mixture at room temperature for 24 h, the precipitate was isolated by filtration, washed with methanol (3×5 mL), and dried at reduced pressure for 18 h to give poly(ethylene:hexamethylene D-glucaramide) (1:4) hydroxypolyamide product (0.70 g, 71%).

Example 3

Poly(4'-aza-4'-methylheptamethylene:hexamethylene D-glucaramide) (2:3) Hydroxypolyamide Product Step 1. Hexamethylenediammonium D-Glucarate and 4'-Aza-4'-methylheptamethylenediammonium D-Glucarate. See method for Step 1, Example 1.

Step 2. Poly(4'-aza-4'-methylheptamethylene:hexamethylene D-glucaramide) (2:3) Hydroxypolyamide Product. Acetyl chloride (1.0 mL, 14 mmol) was added dropwise to methanol (25 mL) at 0° C. The solution was allowed to warm to room temperature (10 min) before 4'-aza-4'-methylheptamethylenediammonium D-glucarate (0.50 g, 1.4 mmol) and hexamethylenediammonium D-glucarate (0.69 g, 2.1 mmol) were added. The solution was stirred for 3 h at room temperature then concentrated to a solid. After drying at reduced pressure for 18 h, the solid was re-dissolved in methanol (10 mL). Sodium methoxide solution (13 mL, 6.5 mmol) and triethylamine (0.25 mL, 1.8 mmol) were added to the methanol solution, and a precipitate was observed within 45 min. After stirring the mixture at room temperature for 24 h, the precipitate was isolated by filtration, washed with methanol (3×5 mL), and dried at reduced pressure for 18 h to give poly(4'-aza-4'-methylheptamethylene:hexamethylene D-glucaramide) (2:3)hydroxypolyamide product (0.54 g, 49%).

Example 4

Poly(tris[ethylene]amino:hexamethylene D-glucaramide) (1:4) Hydroxypolyamide Product Step 1a. Tris(ethyleneammonium)amino D-glucarate. Acid form cation exchange resin (8.0 mL, 17 mmol, Dowex 50WX8-100, 2.1 meq/mL) was washed with deionized water (3×15 mL). Monopotassium D-glucarate (2.49 g, 10.0 mmol) was added to a slurry of the washed resin in water (20 mL), and the mixture was agitated for 10 min. The resin was removed by filtration and washed with water (3×10 mL). Tris(2-aminoethyl)amine (1.0 mL, 6.7 mmol) was added to the combined filtrate and washings, and the resulting solution was stirred for 3 h then concentrated to a viscous syrup. Methanol (20 mL) was added to the syrup, and the mixture was stirred until all of the oil precipitated as a fine, white solid (18 h). The precipitate was isolated by filtration, washed with methanol (3×5 mL) and dried at reduced pressure for 18 h to tris[ethyleneammonium]amino D-glucarate (2.77 g, 90%).

Step 1b. Hexamethylenediammonium D-Glucarate. See method for Step 1, Example 1.

Step 2. Poly(tris[ethylene]amino:hexamethylene D-glucaramide) (1:4) Hydroxypolyamide Product. Acetyl chloride (1.0 mL, 14 mmol) was added dropwise to methanol (25 mL) at 0° C. The solution was allowed to warm to room temperature (10 min) before tris(ethyleneammonium)amino D-glucarate (0.32 g, 0.70 mmol) and hexamethylenediammonium D-glucarate (0.92 g, 2.8 mmol) were added. The solution was stirred for 3 h at room temperature then concentrated to a solid. After drying at reduced pressure for 18 h, the solid was re-dissolved in methanol (11 mL). Sodium methoxide solution (14 mL, 7.0 mmol) and triethylamine (0.49 mL, 3.5 mmol) were added to the methanol solution, and a precipitate was observed within 5 min. After stirring the mixture at room temperature for 24 h, the precipitate was isolated by filtration, washed with methanol (3×5 mL), and dried at reduced pressure for 18 h to give poly(tris[ethylene]amino:hexamethylene D-glucaramide) (1:4) polyhydroxypolyamide product (0.75 g, 68%).

Representative Synthesis of a Poly($C_x$:$A_m$:$A_n$) Hydroxypolyamide Product. $A_m$ and $A_n$ represent a range of acyclic or cyclic alkylene units or acylic alkylene units or alkylated or otherwise substituted alkylene units, and/or alkylene units replaced by one or more hetero atoms (e.g., N, O, P, or S, etc.), and/or arylalkyl units with pendant unsubstituted and/or alkylated or otherwise substituted methylene units, and/or a carbocylic or heterocyclic units of varying structure with pendant unsubstituted and/or alkylated or otherwise substituted methylene units. The methylene units, substituted or otherwise unsubstituted, are each connected to a carbonyl carbon atom of an amide unit in the polyamide.

Example 5

Poly(hexamethylene xylaramide:D-glucaramide) (1:6) Hydroxypolyamide Product

Step 1a. Hexamethylenediammonium Xylarate. A methanol solution of hexamethylenediamine (110 mL, 0.5 M) was added to a methanol solution of xylaric acid (100 mL, 0.5 M). The precipitate, which rapidly formed, was stirred for 3 h then isolated by filtration, washed with methanol, and dried at reduced pressure to yield hexamethylenediammonium xylarate (13.33 g, 90%).

Step 1b. Hexamethylenediammonium D-Glucarate. See method for Step 1, Example 1.

Step 2. Poly(hexamethylene xylaramide:D-glucaramide) (1:6) Hydroxypolyamide Product. Acetyl chloride (2.0 mL, 28 mmol) was added dropwise to methanol (50 mL) at 0° C. The solution was allowed to warm to room temperature (10 min) before hexamethylenediammonium xylarate (0.31 g, 1.0 mmol) and hexamethylenediammonium D-glucarate (1.95 g, 5.97 mmol) were added. The solution was stirred for 3 h at room temperature then concentrated to a solid. After drying at reduced pressure for 18 h, the solid was re-dissolved in methanol (24 mL). Sodium methoxide solution (26 mL, 13 mmol) and triethylamine (0.49 mL, 3.5 mmol) were added to the methanol solution, and a precipitate was observed within 20 min. After stirring the mixture at room temperature for 24 h, the precipitate was isolated by filtration, washed with methanol (3×5 mL), and dried at reduced pressure for 18 h to give poly(hexamethylene xylaramide:D-glucaramide) (1:6) hydroxypolyamide product (1.51 g, 60%).

Representative Synthesis of a Poly($C_x$:$C_y$/$A_m$:$A_n$) Hydroxypolyamide Product.

Example 6

Poly(tetramethylene:hexamethylene/xylaramide:D-glucaramide) (1:4) Hydroxypolyamide Product Step 1a. Tetramethylenediammonium Xylarate. See method for Step 1, Example 1.

Step 1b. Hexamethylenediammonium D-Glucarate. See method for Step 1, Example 1.

Step 2. Poly(tetramethylene:hexamethylene/xylaramide: D-glucaramide) (1:4/1:4) Hydroxypolyamide Product. Acetyl chloride (2.0 mL, 28 mmol) was added dropwise to methanol (50 mL) at 0° C. The solution was allowed to warm to room temperature (10 min) before tetramethylenediammonium xylarate (0.38 g, 1.5 mmol) and hexamethylenediammonium D-glucarate (1.83 g, 5.62 mmol) were added. The solution was stirred for 3 h at room temperature then concentrated to a solid. After drying at reduced pressure for 18 h, the solid was re-dissolved in methanol (24 mL). Sodium methoxide solution (26 mL, 13 mmol) and triethylamine (0.49 mL, 3.5 mmol) were added to the methanol solution, and a precipitate was observed within 30 min. After stirring the mixture at room temperature for 24 h, the precipitate was isolated by filtration, washed with methanol (3×5 mL), and dried at reduced pressure for 18 h to give poly(tetramethylene:hexamethylene/xylaramide:D-glucaramide) (1:4/1:4) hydroxypolyamide product (1.32 g, 68%).

Representative Example Synthesis of a Hydroxypolyamide from a Carboxyl Group Activated Aldarate and an Alkylenediamine, a Substituted Alkylenediamine, or an Alkylenediamine with One or More Methylene Units of the Alkylene Unit Replaced by One or More Hetero Atoms.

Example 7

Poly(hexamethylene D-glucaramide) Hydroxypolyamide

Poly(hexamethylene D-glucaramide) Hydroxypolyamide. Hexamethylenediamine (HMDA) (0.21 g, 1.8 mmol) was added to methyl D-glucarate 1,4-lactone (0.35 g, 1.7 mmol) dissolved in methanol (25 mL). The solution became cloudy within 15 min. After stirring for 24 h, the solid polymer was isolated by filtration, washed with methanol (3×5 mL), and dried at reduced pressure for 18 h to give poly(hexamethylene D-glucaramide) hydroxypolyamide (0.34 g, 69%).

Example 8

Poly[sodium-2-carboxylate-pentamethylene/hexamethylene D-glucaramide] (1:3) Hydroxypolyamide Poly[sodium (S)-2-carboxylate-pentamethylene/hexamethylene D-glucaramide] (1:3) Hydroxypolyamide. Sodium methoxide solution (4.6 mL, 2.3 mmol) was added to L-lysine monohydrochloride (0.21 g, 1.1 mmol) suspended in methanol (20 mL). Upon dissolution of the solid, methyl D-glucarate 1,4-lactone (0.94 g, 4.6 mmol) was added. The solution became cloudy within 25 min. After 2 h, hexamethylenediamine (0.40 g, 3.4 mmol) in methanol (25 mL) was added to the mixture. More precipitate formed rapidly. After stirring for 24 h, the solid polymer was isolated by filtration, washed with methanol (3×20 mL), and dried at reduced pressure for 18 h to give poly[sodium (S)-2-carboxylate-pentamethylene/hexamethylene D-glucaramide] (1:3) hydroxypolyamide (1.15 g, 82%).

Representative Example Synthesis of Charged Hydroxypolyamides, Hydroxypolyamide Products, or Post-Hydroxypolyamides.

Example 9

Poly(4'-aza-4'-methylheptamethylene:hexamethylene D-glucaramide) (2:3) Hydroxypolyamide Hydrochloride Salt Poly(4'-aza-4'-methylheptamethylene:hexamethylene D-glucaramide) (2:3) Hydroxypolyamide Hydrochloride Salt. Poly(4'-aza-4'-methylheptamethylene:hexamethylene D-glucaramide) (2:3) hydroxypolyamide (0.11 g) was dissolved in H₂O (2 mL). To the resulting solution (pH 9) was added aqueous HCl (0.14 mL, 1.0 M). The solution (pH 2) was stirred for 15 min then concentrated to a clear film. The film was triturated with methanol and dried at reduced pressure for 18 h to give poly(4'-aza-4'-methylheptamethylene:hexamethylene D-glucaramide) (2:3) hydroxypolyamide hydrochloride salt (0.064 g) as a white, amorphous solid.

Representative Example Synthesis of a Post-Hydroxypolyamide.

Example 10

Poly(hexamethylene D-glucaramide) Post-Hydroxypolyamide

Poly(hexamethylene D-glucaramide) Post-Hydroxypolyamide. Ethylene glycol (4.5 mL) and triethylamine (0.75 mL) were added to poly(hexamethylene D-glucaramide) hydroxypolyamide (0.50 g) dissolved in dimethyl sulfoxide (DMSO) (4.5 mL) at 60° C. The solution became cloudy within 15 min. After stirring at 60° C. for 18 h, the mixture was diluted with methanol (15 mL) and allowed to cool to room temperature. The resulting precipitate was isolated by filtration, washed with methanol (3×5 mL) and dried at reduced pressure for 18 h to give poly(hexamethylene D-glucaramide) post-hydroxypolyamide (0.41 g, 82%).

Example 11

Poly(tetramethylene:hexamethylene D-glucaramide) (1:1) Post-Hydroxypolyamide

Poly(tetramethylene:hexamethylene D-glucaramide) (1:1) Post-Hydroxypolyamide. Ethylene glycol (0.9 mL) and triethylamine (0.15 mL) were added to poly(tetramethylene: hexamethylene D-glucaramide) (1:1) hydroxypolyamide (0.10 g) dissolved in dimethyl sulfoxide (DMSO) (0.9 mL) at 60° C. After stirring at 60° C. for 18 h, the mixture was diluted with methanol (15 mL) and allowed to cool to room temperature. The resulting precipitate was isolated by filtration, washed with methanol (3×5 mL) and dried at reduced pressure for 18 h to give poly(tetramethylene: hexamethylene D-glucaramide) (1:1) post-hydroxypolyamide (0.06 g, 60%).
Representative Examples of Gel Preparation with Hydroxypolyamides, Hydroxypolyamide Products, or Post-Hydroxypolyamides.

Example 12

Hydrogel Preparation with Poly(hexamethylene D-glucaramide) Hydroxypolyamide

Water (0.95 mL) was added to poly(hexamethylene D-glucaramide) hydroxypolyamide (7.5 mg) dissolved in DMSO (0.05 mL). After brief mixing, the solution was allowed to sit undisturbed. Cloudiness developed rapidly, and an opaque gel formed, typically, within 10 min.

Example 13

Hydrogel Preparation with Poly(hexamethylene D-glucaramide) Post-Hydroxypolyamide and Sodium Chloride Poly(hexamethylene D-glucaramide) post-hydroxypolyamide (7.6 mg) was dissolved in DMSO (0.05 mL). Sodium chloride (4.5 mg) was added to the solution followed by water (0.95 mL). After brief mixing to dissolve the sodium chloride, the solution was allowed to sit undisturbed. Cloudiness developed rapidly, and an opaque gel formed within 10 min.

Example 14

Organogel Preparation with Poly(hexamethylene D-glucaramide) Hydroxypolyamide

Poly(hexamethylene D-glucaramide) hydroxypolyamide (25 mg) was dissolved in ethylene glycol (1 mL) with heat (70-80° C.). The resulting solution was allowed to cool to room temperature undisturbed. Cloudiness developed after several minutes, and an opaque gel formed within 10 min.

Example 15

Hydrogel Preparation with Poly(ethylene:hexamethylene D-glucaramide) Hydroxypolyamide Poly(ethylene:hexamethylene D-glucaramide) (1:4) hydroxypolyamide (7.5 mg) was dissolved in water with heat (70-80° C.). The solution was allowed to sit undisturbed, and a clear gel formed over several hours.
Representative Examples of pH Dependent Gel Formation with Hydroxypolyamides, Hydroxypolyamide Products, or Post-Hydroxypolyamides.

Example 16 pH Dependent Hydrogel Preparation with Poly(4'-aza-4'-methylheptamethylene:hexamethylene D-glucaramide) (1:1) Hydroxypolyamide Aqueous HCl (0.28 mL, 0.1 M) was added to poly(4'-aza-4'-methylheptamethylene:hexamethylene D-glucaramide) (1:1) hydroxypolyamide (25 mg) suspended in H$_2$O (0.16 mL). To the resulting solution (pH 2) was added aqueous NaOH (0.42 mL, 0.1 M). After brief mixing, the solution (pH 8) was allowed to sit undisturbed, and a clear gel formed over several hours.

Example 17 pH Dependent Hydrogel Preparation with Poly(4'-aza-4'-methylheptamethylene:hexamethylene D-glucaramide) Hydroxypolyamide Hydrochloride Salt Poly(4'-aza-4'-methylheptamethylene:hexamethylene D-glucaramide) (2:3) hydroxypolyamide hydrochloride salt (10 mg) was dissolved in water (0.25 mL) at room temperature. To the resulting solution (pH 4), aqueous sodium carbonate (0.75 mL, 1% wgt/vol) was added. After brief mixing, the resulting solution (pH 10) was allowed to sit undisturbed, and a clear gel formed over several hours.
Representative Examples of Gel Formation with Hydroxypolyamide, Hydroxypolyamide Products, or Post-Hydroxypolyamides in Aqueous Salt Solutions.

Example 18

Hydrogel Preparation with Poly(ethylene:hexamethylene D-glucaramide) Hydroxypolyamide and Human Urine Poly(ethylene/hexamethylene D-glucaramide) (1:2) hydroxypolyamide (20 mg) was dissolved in human urine (1 mL) with heat (70-80° C.). The solution was allowed to sit undisturbed, and a slightly opaque gel formed over several hours.

Example 19

Hydrogel Preparation with Poly(4'-aza-4'-methylheptamethylene:hexamethylene D-glucaramide) Hydroxypolyamide and Potassium Nitrate Solution Poly(4'-aza-4'-methylheptamethylene:hexamethylene D-glucaramide) (1:3) hydroxypolyamide (20 mg) was dissolved in 3% (wgt/vol) potassium nitrate solution (1 mL)

with heat (70-80° C.). The solution was allowed to sit undisturbed, and a slightly opaque gel formed within 45 min.

Example 20

Hydrogel Preparation with Poly(tetramethylene:hexamethylene D-glucaramide) Hydroxypolyamide and Monobasic Potassium Phosphate/Potassium Nitrate Solution Poly(tetramethylene:hexamethylene D-glucaramide) (1:2) hydroxypolyamide (20 mg) was dissolved in 2% (wgt/vol) monobasic potassium phosphate/1% (wgt/vol) potassium nitrate solution (1 mL) with heat (70-80° C.). The solution was allowed to sit undisturbed, and a slightly opaque formed within 45 min.

TABLE 1

Comparison of gel forming ability of poly(hexamethylene D-glucaramide) hydroxypolyamides, hydroxypolyamide products, and post-hydroxypolyamides prepared by different methods in various liquid mediums.

| Gel Forming Agent | Hydroxypolyamide Preparation Method | Liquid Medium | Gel Forming Ability[a] |
|---|---|---|---|
| HPA[b] | Esterified glucarate and HMDA[b] | 5% DMSO/$H_2O$[c] | Good |
| HPA + NaCl[d] | Esterified glucarate and HMDA | 5% DMSO/$H_2O$[e] | Good |
| Pre-HPA[f] | Disalt - $Et_3N$[f] | 5% DMSO/$H_2O$ | Good |
| Pre-HPA + NaCl | Disalt - $Et_3N$ | 5% DMSO/$H_2O$ | Good |
| HPAP[g] | Disalt - NaOMe[g] | 5% DMSO/$H_2O$ | Very good |
| HPAP + NaCl | Disalt - NaOMe | 5% DMSO/$H_2O$ | Very good |
| HPAP | Disalt - NaOMe | 10% DMSO/$H_2O$ | Very good |
| HPAP | Disalt - NaOMe | 15% DMSO/$H_2O$ | Very good |
| HPAP | Disalt - NaOMe | 20% DMSO/$H_2O$ | Very good |
| HPAP | Disalt - NaOMe | 25% DMSO/$H_2O$ | Very good |
| HPAP | Disalt - NaOMe | Ethylene glycol[h] | Moderate |
| Post-HPA[i] | Esterified glucarate and HMDA | 5% DMSO/$H_2O$ | Good |
| Post-HPA + NaCl | Esterified glucarate and HMDA | 5% DMSO/$H_2O$ | Good |
| Post-HPA | Disalt - $Et_3N$ | 5% DMSO/$H_2O$ | Good |
| Post-HPA + NaCl | Disalt - $Et_3N$ | 5% DMSO/$H_2O$ | Good |
| Post-HPA | Disalt - NaOMe | 5% DMSO/$H_2O$ | Good |
| Post-HPA + NaCl | Disalt - NaOMe | 5% DMSO/$H_2O$ | Good |

[a]Based on the minimum concentration (wgt/vol %) of polyhydroxypolyamide required to form a gel in solution. Very good—≤0.75%; Good—0.8 to 1.5%; Moderate—1.6 to 5.0%.
[b]Hydroxypolyamide (HPA) synthesis described in Example 7 and Kiely, 1994.
[c]Gel preparation described in Example 12.
[d]Poly(hexamethylene D-glucaramide) plus added sodium chloride (3-5 mg).
[e]Gel preparation described in Example 13.
[f]Pre-Hydroxypolyamide (Pre-HPA) synthesis described in U.S. Pat. No. 6,894,135 B2.
[g]Hydroxypolyamide product (HPAP) synthesis described in Example 1
[h]Gel preparation described in Example 14.
[i]Post-hydroxypolyamide (Post-HPA) synthesis described in Example 10 and U.S. Pat. No. 6,894,135 B2.

TABLE 2

Hydrogel forming ability of poly($C_x$:$C_y$ D-glucaramide) hydroxypolyamide products derived from one polyacid and two polyamines.

| $C_x$:$C_y$ Components | $C_x$:$C_y$ Ratio | Gel Forming Ability[a,b] |
|---|---|---|
| $C_2$:$C_6$[c] | 1:5 | Good |
| $C_2$:$C_6$ | 1:4 | Very good |
| $C_2$:$C_6$ | 1:3 | Good |
| $C_2$:$C_6$ | 1:2 | Good |
| $C_4$:$C_6$[d] | 1:3 | Very good |
| $C_4$:$C_6$ | 1:2 | Very good |

TABLE 2-continued

Hydrogel forming ability of poly($C_x$:$C_y$ D-glucaramide) hydroxypolyamide products derived from one polyacid and two polyamines.

| $C_x$:$C_y$ Components | $C_x$:$C_y$ Ratio | Gel Forming Ability[a,b] |
|---|---|---|
| $C_4$:$C_6$ | 1:1 | Good |
| $NC_1$:$C_6$[e] | 1:4 | Very good |
| $NC_1$:$C_6$ | 1:3 | Very good |
| $NC_1$:$C_6$ | 1:2 | Good |
| $NC_1$:$C_6$ | 2:3 | Good |
| $NC_1$:$C_6$ | 1:1 | Good |
| Dioxa:$C_6$[f] | 1:2 | Very good |
| TREN:$C_6$[g] | 1:4 | Good |
| 2MeC$_5$:$C_6$[h] | 1:1 | Very Good |
| K:$C_6$[i] | 1:3 | Moderate |
| $C_4$:$C_8$[j] | 1:1 | Moderate |
| $C_4$:$C_8$ | 2:1 | Moderate |
| $C_4$:$C_8$ | 3:1 | Moderate |
| $C_4$:$C_{12}$[k] | 4:1 | Moderate |

[a]Gel preparation described in Example 15
[b]See Gel Forming Ability, Table 1
[c]Ethylene:hexamethylene
[d]Tetramethylene:hexamethylene
[e]4'-Aza-4'-methylheptamethylene:hexamethylene
[f]3',6'-Dioxaoctamethylene:hexamethylene
[g]3'-Aza-3'-ethylenepentamethylene:hexamethylene
[h]2-Methylpentamethylene:hexamethylene
[i]Sodium (S)-2-carboxylate-pentamethylene:hexamethylene
[j]Tetramethylene:octamethylene
[k]Tetramethylene:dodecamethylene

TABLE 3

Gel forming ability of poly($C_x$:$C_y$/$A_m$:$A_n$) hydroxypolyamide products derived from two polyamines and two polyacids.

| $C_x$:$C_y$ Components | $C_x$:$C_y$ Ratio | $A_m$:$A_n$ Components | $A_m$:$A_n$ Ratio | Liquid Medium | Gel Forming Ability[a] |
|---|---|---|---|---|---|
| $C_6$ | 1:1 | Xyl:Glu[d] | 1:6 | 5% DMSO/$H_2O$[b] | Good |
| $C_4$:$C_6$ | 1:4 | Xyl:Glu[d] | 1:4 | $H_2O$[e] | Very good |

[a]See Gel Forming Ability, Table 1.
[b]Gel preparation described in Example 12.
[c]Tetramethylene:hexamethylene.
[d]Xylaramide:D-glucaramide.
[e]Gel preparation described in Example 15.

It is understood that the foregoing examples are merely illustrative of the present invention. Certain modifications of the articles and/or methods employed may be made and still achieve the objectives of the invention. Such modifications are contemplated as within the scope of the claimed invention.

REFERENCES

F. L. Buchholz and N. A. Peppas, Eds.; Superabsorbent Polymers: Science and Technology, ACS Symposium Series, No. 573, Oxford University Press, 1994.

F. L. Buchholz and A. T. Graham, Eds.; Modern Superabsorbent Polymer Technology, John Wiley & Sons, 1998.

(b) F. L. Buchholz, Superabsorbent Polymers: An Idea Whose Time Has Come. J. Chem. Educ., 73, 512-515, 1996.

B. Jeong, Y. H. Bae, D. S. Lee, and S. W. Kim, Biodegradable block copolymers as injectable drug-delivery systems. Nature, 388, 860-862, 1997.

H. A. von Recum, S. W. Kim, A. Kikuchi, M. Okuhara, Y. Sakurai, and T. Okano, Novel thermally reversible hydrogel as detachable cell culture substrate. J. Biomed. Mater. Res., 40, 631-639, 1998.

J. Kisiday, M. Jin, B. Kurz, H. Hung, C. Semino, S. Zhang, and A. J. Grodzinsky, Self-assembling peptide hydrogel fosters chondrocyte extracellular matrix production and cell division: Implications for cartilage tissue repair. *PNAS,* 99, 9996-10001, 2002.

K. Y. Lee and D. J. Mooney, Hydrogels for tissue engineering. *Chem. Rev.,* 101, 1869-1879, 2001.

A. Hüttermann, M. Zommorodi, and K. Reise, Addition of hydrogels to soil for prolonging the survival of *Pinus halepenis* seedlings subjected to drought. *Soil and Tillage Res.,* 50, 295-304, 1999.

E. Karadağ, D. Saraydin, Y. Caldiran, and O. Güven, Swelling studies of copolymeric acrylamide/crotonic acid hydrogels as carriers for agricultural uses. *Polym. Adv. Technol.,* 11, 59-68, 2000.

W. E. Rudziniski, A. M. Dave, U. H. Vaishnav, S. G. Kumbar, A. R. Kulkarni, and T. M. Aminabhavi, Hydrogels as controlled release devices in agriculture. *Des. Monomers Polym.,* 5, 39-65, 2002.

D. E. Kiely, K. Kramer, and J. Zhang, U.S. Pat. No. 6,894,135 B2, filed Dec. 10, 2003, issued May 17, 2005, Method for preparing high molecular weight random polyhydroxypolyamides.

T. Jahns, D. E. Kiely, Abiotic Hydrolysis of Some Poly-D-Glucaramides and Subsequent Microbial Utilization/Degradation. *J. Polym. Environ.* 14, 165-169, 2006.

D. E. Kiely, L. Chen and T-H Lin, Hydroxylated nylons based on unprotected esterified D-glucaric acid by simple condensation reactions. *J. Am. Chem. Soc.,* 116, 571-578, 1994.

D. E. Kiely and T-H Lin, U.S. Pat. No. 4,833,230, filed Jun. 21, 1988, issued May 23, 1989, Polyhydroxypolyamides and process for making same.

T. N. Smith and D. E. Kiely, Process for higher molecular weight stereo-random polyhydroxypolyamides from D-glucaric acid, American Chemical Society 231$^{st}$ National Meeting, Atlanta, Ga., March 2006, CARB 54.

T. N. Smith, T. T. Denton, J. Zhang, K. Kramer, and D. E. Kiely, Synthesis and Characterization of Higher Molecular Weight Stereo-Random Poly(D-glucaramides) from 1:1 Alkylenediammonium D-Glucaric Acid, American Chemical Society 234$^{th}$ National Meeting, Boston, Mass., August 2007, I&EC 24.

D. E. Kiely, L. Chen, and D. W. Morton, U.S. Pat. No. 5,434,233, filed May 24, 1994, issued Jul. 18, 1995, Polyaldaramide Polymers Useful For Films and Adhesives.

D. W. Morton and D. E. Kiely, Evaluation of the Film and Adhesive Properties of Some Block Copolymer Polyhydroxypolyamides from Esterified Aldaric Acids and Diamines. *J. Appl. Polym. Sci.* 17, 3085-3092, 2000.

What is claimed is:

1. A process for making a hydroxypolyamide product comprising a hydroxypolyamide component and a salt component, each component produced in the same polymerization process, the process comprising the steps of:
   a) forming a stoichiometrically molar balanced (1:1) organic polyacid:polyamine salt from an organic polyacid and polyamine, wherein the organic polyacid is derived from at least one organic polyacid having at least one pendant hydroxyl group, and wherein the one polyamine is derived from at least one organic polyamine;
   b) esterifying the carboxylate portion of the organic polyacid:polyamine salt in an alcohol with an acid source and converting the polyamine portion to a polyamine salt of the acid source; and
   c) treating the esterified organic polyacid:polyamine salt in a solvent with base, wherein the base is stronger than a tertiary amine, to form a hydroxypolyamide product, wherein the minimum concentration (wgt/vol %) of the hydroxypolyamide product required to form a gel in solution is 0.75%.

2. A process in accordance with claim 1, wherein said organic polyacid having at least one pendant hydroxyl group is selected from the group consisting of: aliphatic polyacids, carbocyclic polyacids, heterocyclic polyacids, arylalkyl polyacids; said polyacids with at least one substituent selected from group consisting of alkyl, alkenyl, and alkynyl groups, substituted alkyl, alkenyl, and alkynyl groups, aryl groups and/or substituted aryl groups, other groups, atoms other than hydrogen; said polyacids with at least one hetero atom in place of at least one carbon atom; said polyacids substituted with at least one pendant group selected from the group consisting of ester, ether, ketone, thiol, thioether, nitro, nitrile, and cyano.

3. A process in accordance with claim 1, wherein said organic polyacid having at least one pendant hydroxyl group is selected from the group consisting of: tartronic acid; tartaric acids; xylaric acid; arabinaric acids; ribaric acid; lyxaric acids; glucaric acids; mannaric acids; galactaric acid; idaric acids; and citric acid.

4. A process in accordance with claim 1, wherein said organic polyamine is selected from the group consisting of: alkylenepolyamines; alkenylenepolyamines; alkynylenepolyamines; alkylarylpolyamines; alkenylarylpolyamines; alkynylarylpolyamines; carbocyclic polyamines; heterocylic polyamines; said polyamines substituted with at least one alkyl, alkenyl, and alkynyl groups, substituted alkyl, alkenyl, and alkynyl groups, aryl groups and substituted aryl groups, other groups, atoms other than hydrogen; said polyamines with at least one hetero atom in place of at least one carbon atom; said polyamines substituted with at least one pendant group selected from the group consisting of alcohol, ester, ether, ketone, thiol, thioether, nitro, nitrile, and cyano.

5. A process in accordance with claim 1, wherein said organic polyamine is selected from the group consisting of: ethylenediamine, tetramethylenediamine, pentamethylenediamine, hexamethylenediamine, heptamethylenediamine, octamethylenediamine, decamethylenediamine, dodecamethylenediamine, 2-methylpentamethylenediamine, methylheptamethylenediamine, 3',6'-dioxaoctamethylenediamine, L-lysine, and tris(2-aminoethyl)amine.

6. A process in accordance with claim 1 wherein said alcohol is selected from the group consisting of methanol, ethanol, 2-propanol, 1-propanol, t-butyl alcohol, 1-butanol, and 1-hexanol.

7. A process in accordance with claim 1 wherein said acid source is a mineral acid selected from the group consisting of hydrochloric acid, hydrobromic acid, hydrofluoric acid, phosphoric acid, and sulfuric acid.

8. A process in accordance with claim 1 wherein said solvent is selected from the group consisting of methanol, ethanol, 2-propanol, 1-propanol, 1-butanol, t-butyl alcohol, sec-butanol, 1-pentanol, 2-pentanol, 3-pentanol, 2-methyl-1-butanol, 1-hexanol, 2-hexanol, 3-hexanol, ethylene glycol, glycerol, dimethoxyethane, diglyme, dimethylformamide, acetonitrile, N-methylpyrrolidone, and dimethyl sulfoxide.

9. A process in accordance with claim 1 wherein said base stronger than a tertiary amine is a metal alkoxide comprising:
   a) a metal cation selected from the group consisting of sodium, potassium, lithium, calcium, and magnesium; and
   b) an alkoxide derived from an alcohol selected from the group consisting of methanol, ethanol, 2-propanol, 1-propanol, t-butyl alcohol, 1-butanol, and 1-hexanol.

* * * * *